United States Patent [19]
Grant et al.

[11] Patent Number: 5,624,815
[45] Date of Patent: Apr. 29, 1997

[54] METHOD AND APPARATUS FOR THE ANALYSIS OF BIOLOGICAL MATERIAL

[75] Inventors: Peter L. Grant, Cambridgeshire; Nicholas P. M. Foote; Michael Noble, both of Cambridge; Christopher T. Evans, Hertfordshire, all of Great Britain

[73] Assignee: Celsis International plc, Cambridge, United Kingdom

[21] Appl. No.: 302,905

[22] PCT Filed: Mar. 22, 1993

[86] PCT No.: PCT/GB93/00577

§ 371 Date: Dec. 5, 1994

§ 102(e) Date: Dec. 5, 1994

[87] PCT Pub. No.: WO93/19199

PCT Pub. Date: Sep. 30, 1993

[30] Foreign Application Priority Data

| Mar. 20, 1992 | [GB] | United Kingdom | 9206124 |
| Mar. 20, 1992 | [GB] | United Kingdom | 9206143 |
| Mar. 20, 1992 | [GB] | United Kingdom | 9206147 |
| Jun. 24, 1992 | [GB] | United Kingdom | 9213444 |

[51] Int. Cl.$^6$ ............................. C12Q 1/24; C12Q 1/08; C12M 1/34; C12M 1/12
[52] U.S. Cl. ............................. 435/30; 435/6; 435/40; 435/287.2; 435/288.4; 435/297.5; 210/405; 210/456; 73/61.72; 73/863.23; 422/101
[58] Field of Search ............................. 435/30, 29, 34, 435/39, 40, 287.1, 287.9, 287.2, 288.4, 288.5, 305.1, 297.5, 305.2, 305.3, 308.1, 4, 6; 422/99, 101, 102, 100; 210/405, 406, 456; 141/237, 240; 436/63, 94, 177; 73/64.56, 61.71, 61.72, 863.21, 863.23

[56] References Cited

U.S. PATENT DOCUMENTS

| 3,929,583 | 12/1975 | Sharpe et al. | 195/127 |
| 4,018,652 | 4/1977 | Lanham et al. | 195/103.5 |
| 4,055,202 | 10/1977 | Greene | 141/237 |
| 4,294,931 | 10/1981 | Levin et al. | 422/102 |
| 4,493,815 | 1/1985 | Fernwood et al. | 422/101 |
| 5,096,676 | 3/1992 | McPherson et al. | 422/102 |
| 5,306,420 | 4/1994 | Bisconte | 435/308.1 |

FOREIGN PATENT DOCUMENTS

| 0128527 | 12/1984 | European Pat. Off. | C12Q 1/18 |
| 2649411 | 1/1991 | France | C12Q 1/06 |
| 60-135862 | 7/1985 | Japan | G01N 33/48 |
| 4-104799 | 4/1992 | Japan | 435/39 |
| 2035372 | 6/1980 | United Kingdom | C12Q 1/10 |
| WO8202561 | 8/1982 | WIPO | C12Q 1/18 |
| 91/11245 | 8/1991 | WIPO . | |

OTHER PUBLICATIONS

Annals of the New York Academy of Sciences, vol. 501, 1987, pp. 350-353, G.B. Williams et al., Rapid detection of E. coli immobilized in gel microdroplets.

Primary Examiner—William H. Beisner
Attorney, Agent, or Firm—George W. Rauchfuss, Jr.

[57] ABSTRACT

A method for analyzing solid material in a liquid sample comprises the steps of: distributing the sample equally by passage through a number of discrete wells adapted to retain the solid material, the concentration of solid material being such that it is absent in at least one well; and analyzing the wells for the presence of retained solid material. A device adapted for use in a method for analyzing solid material in a liquid sample comprises the combination of: a container for the sample; a unit comprising a number of discrete wells adapted to retain the solid material and allow the passage of liquid under the application of reduced pressure; structure for drawing liquid from the container and through the wells under reduced pressure; and a manifold or other element that provides uniform distribution of the sample passing from the container into the wells.

17 Claims, 2 Drawing Sheets

METHOD AND APPARATUS FOR THE ANALYSIS OF BIOLOGICAL MATERIAL

FIELD OF THE INVENTION

This invention relates to a method of analysis, e.g. for enumerating and/or identifying microorganisms or other biological material in a liquid sample, and to apparatus for use in such a method.

BACKGROUND OF THE INVENTION

Many industries, including pharmaceuticals, need to detect low levels of materials in large volumes of liquid. For example, they rely heavily on classical microbiological techniques to detect microbial contamination. Areas often under surveillance by Quality Assurance personnel include the control of bioburden in incoming raw materials, especially liquids; monitoring of microbial population in the production environment; in-process controls, especially after storage; and final product testing. Often product is manufactured and stored whilst analysis for microbial content takes place. If contamination is detected, the product may need to be destroyed, and the production line shut down until the source of contamination is found. Often the time taken for microbial analysis is the rate-limiting factor in bringing the plant on stream. This can lead to substantial costs in wasted production or raw materials.

The determination of the number of microorganisms present in the various types of water used in a pharmaceutical environment is considered a critical factor in producing many products. Usually, the microbiological specification ranges from 0.01 to 100 cfu per ml of water, depending on the source of the sample.

Classical methods of microbe detection, whilst considered reliable and accepted in the industry, are slow and require valuable storage and laboratory space.

A test for coliform bacilli is described in "Handbook of Practical Bacteriology" 9 (1956), by T. J. Mackie and J. E. McCartney, pub. E. and S. Livingstone. The method employs a specific medium which is utilised by coliforms to release acid, and thus to give a colour change with a pH indicator. Several tubes are set up, at different dilutions, and a McCrady table is used to determine the most probable number of bacilli, from the number of positives detected. This method allows the detection of small numbers of microbes in a large volume of liquid, but involves serial dilution and an incubation stage of 48 hours.

Cherwell Laboratories Ltd., Bicester, UK, and Wilkinson and Simpson Ltd., Gateshead, UK, each produce test kits, respectively under the trade names Colitrace and Colilert, designed to test water for levels of selected organisms down to 1 per 100 ml of sample. The sample is distributed between independent tubes containing culture broths, which are then incubated; the presence of coliforms is indicated by a colour change, and *E. coli* can be detected by fluorescence. The most probable number (MPN) test is then used to estimate numbers of organisms.

WO-A-8202561 and also Williams et al, Annals of the New York Acad. Sci. 501:350–353 (1987), disclose methods for the detection of microorganisms in gel microdroplets with counting, using a flow microfluorimeter. The technique is difficult to operate, for a large volume of sample containing a low number of microbes.

FR-A-2649411 discloses a method for quantitative determination of bacteria, by growing them on a semi-selective medium on a membrane support. The method is unsuitable for distinguishing between species of microorganisms.

GB-A-2035372 discloses a method for quantifying coliform bacilli. In an example, a 5 ml sample is measured at a maximum rate of 0.2 ml/min. This is too slow for large sample volumes.

Pat. Abs. Japan 9(299) (P-408)(2022) (Nov. 27, 1985), equivalent to JP-A-60135862, describes a method in which a serum sample is distributed over 128 wells, and growth medium is then added. The serum titer is assayed by then counting the number of wells which are closed by cell colonies. This technique is not suitable for assaying large sample volumes.

U.S. Pat. No. 3,929,583, and subsequent literature naming A. N. Sharpe as an author, describe membrane filters for enumerating microorganisms. The then novel membrane has a grid pattern imprinted on it, providing as many as 1600 "cells" in which microorganisms can be retained by filtration and grown to form colonies. Each cell has an area smaller than the normal colony size so that, after incubation, each existent colony is uniform in size and shape, and has high visibility. It can then be visualised, and enumerated by the MPN technique. This apparatus is shown to be preferable to conventional membrane filters, in that the latter did not allow a count higher than 400 cfu.

It is desirable, not only to enumerate total units of material in a sample, but also to identify specific types of material. For example, certain strains constituting the species *Escherichia coli* are capable of inducing disease. *E. coli* is therefore regarded as a potential pathogenic organism. Several different groups of diarrhoea-inducing strains are known. The enterotoxigenic *E. Coli* (ETEC) strains produce one or more toxins from the heat-labile and the heat-stable (ST) enterotoxin families. Traditionally, the ST enterotoxin has been detected by means of the infant mouse assay; a less costly and less time-consuming assay is desirable, which does not require animal facilities.

Multi-well plates are widely used in analytical laboratories. Some such plates have a filter material at the base of each well. This may be used to draw liquid through the wells under suction, after (different) samples have been introduced into each well.

SUMMARY OF THE INVENTION

The present invention is based on an understanding of the need for more rapid enumeration of microorganisms or other biological material, in samples containing a very low level of the material. In particular, the present invention allows enumeration without the time-consuming step of growing microorganisms into visible colonies. Further, by contrast with U.S. Pat. No. 3,929,583, it provides a means of identifying the material.

According to a first aspect of the present invention, in a method for analysing microorganisms or other material present in a sample, the sample in liquid form, diluted as necessary, is distributed and passed through a number of discrete wells adapted to retain the material; and the wells are observed for the presence of the material. Then, for enumeration, the number of wells in which the material is present may be determined as a function of the total number of wells. Alternatively, or in addition, the wells are analysed for the presence of a specific material.

According to a second aspect of the invention, novel apparatus comprises the combination of: a container for the sample; a unit comprising a number of discrete wells adapted to retain the material; a receptacle for liquid; means for drawing liquid from the container and through the wells under reduced pressure; and a manifold or other means that provides uniform distribution of the sample passing from the container into the wells.

According to a further aspect of the present invention, a multi-well/microtitre plate is modified by sub-division of the wells, a wall being provided within the well whose height is less than that of the well. Such a multi-well plate, having a filter base, can be used in a method or apparatus of the invention.

DESCRIPTION OF THE INVENTION

The novel apparatus and its use depend on the presence of a plurality of compartments that may be small in volume, individually, but which can accept a large throughput of liquid. The compartments are nevertheless separated by walls, allowing individual analysis of material in the wells. It is the ability to handle large volumes of liquid (in which very small amounts of the material may be present, e.g. a low number of microorganisms) that is one principal distinction of the present invention over the prior art. Another is the fact that distribution can be used to give 0 or 1 unit of material in at least substantially each compartment, thus not only facilitating analysis of the number of units of material in the original sample but also providing homogeneous material in individual compartments, that can be identified.

Means is provided in order to retain the material in the compartment, while allowing the passage of liquid. For example, an immobilised ligand for the material may be introduced, e.g. by chemical reaction on to the compartment walls, and this may be specific for the material to be analysed. Procedures and materials for this purpose are well known in the art. Alternatively, a filter element may be provided in the base of each compartment.

The compartments into which the liquid sample is distributed may be the wells of a multi-well/microtitre plate. Such a plate may be of a type that is commercially-available, including the products that are available with a filter material forming the base of the well, and these are particularly useful if, as is preferred, the sample is to be drawn into the wells under suction.

The total number of wells should be sufficient for any one sample to be analysed with the greatest accuracy that is required. In one plate, there may be, for example; 24, 48 or 96, as in a conventional microtitre plate. This may be used for one sample, or a number of different samples may be tested on one plate. As few as 8 wells may be used for one sample, to give a suitable basis for enumeration or identification in accordance with this invention.

The sample concentration should be such that, after distribution, at least one well should contain no units of the detectable material; no meaningful result is obtained if the material is present in every compartment. The method is thus applied to cases in which observation of the wells indicates that the material is present in some, and not in others.

The material to be analysed may be a liquid, in which case it may be distributed with minimal pre-treatment (e.g. dilution). Alternatively, it may be a solid in which microorganisms may be present or microorganisms collected on a swab or filter, in which case the organisms should be dispersed in a suitable liquid medium.

Microorganisms have been discussed above, and will be discussed below, by way of example only. The invention is applicable to any material that is present at any level in a sample, provided that one unit of the material can be detected. If the initial concentration of the material in the sample is low, it can be distributed directly into the compartments; if high, it can first be diluted appropriately. Dilution will not often be necessary for many environmental samples, e.g. in coliform testing. However, any dilution can be conducted quite quickly, and evidence of retained material may then be detected directly, without further delay.

Alternatively, the material (or evidence of its presence) may be amplified. Thus, levels which are below the sensitivity of a given instrument can be determined by the same instrument, after amplification. Examples of such materials are DNA (which can be amplified by PCR) and substances which give a replicable product on reaction with another substance.

If the material retained in the compartments is to be amplified, in order to facilitate analysis, the amplification means may be introduced after distribution of the sample. If the material comprises microorganisms, a suitable growth medium may be introduced with the sample. Such a medium will be liquid, but the fact that discrete wells are used means that there is no confluence.

After distribution, each compartment either does or does not contain material, e.g. 1 microbe. Amplification can then provide a pure, homogeneous culture which itself is valuable. The probability that a compartment contains a homogeneous culture can readily be calculated. Moreover, the respective compartments may comprise different microbes which can be analysed individually, much more accurately and sensitively than is possible by analysis after amplification of all such material in the original sample. The compartments can be tested with specific probes, and non-specific reactions can be minimised.

DNA or RNA probes, and monoclonal antibodies, are examples of suitable probes. Their binding to material in the compartments can be determined in conventional manner, e.g. by an enzyme-linked immunoassay and/or bioluminescence, utilising known reagents.

An alternative procedure involves observation of a colour change. For this purpose, colorimetric reagents may be introduced into the compartments at any suitable stage, optionally together with a growth enhancer. By suitable choice of materials, a colour reaction may be observed, e.g. pink or light-blue according to the materials. In this case, no machine read-out is necessary.

The presence of microorganisms may be detected by introducing bioluminescence reagents. Such a technique, which is much more sensitive than visual detection of colonies, allows wells containing retained material to be recorded on suitable apparatus much more quickly than when using, say, a membrane with a printed grid pattern. The use of discrete wells also allows colonies to have growth medium removed, and optionally also a wash liquid, suitably under suction, before introducing any substance, such as luciferin-luciferase, that gives a signal in the presence of the material to be analysed.

Whatever procedure is adopted, a digital (binary) read-out may be available in a very short period, e.g. within 24 hours and often much less. This compares favourably with the longer periods that are required by current techniques.

Statistical analysis allows the calculation of probabilities for the enumeration of microbes in, say, a multi-well microplate. The mathematical approach used depends on whether the result required is an estimate of the total number of microbes introduced into the wells, or a value for the most probable number of microbes per unit volume in a bulk sample from which has been taken a sub-sample.

The former approach will generate an integral result, which represents the most likely reason for a particular outcome. For instance, if X compartments out of a total of $\underline{W}$ show positive results, the most likely reason is that $\underline{N}$ microbes were introduced initially. For low values of $\underline{Y}$, $\underline{N}$ will be equal to $\underline{Y}$. For higher values, N will be greater than $\underline{Y}$.

Where it is desired to relate the outcome of a test to the most probable number of microbes per unit volume of a bulk sample, the probabilities involved in the sampling step also have to be taken into account. Equations have been developed which relate the proportion of compartments giving a negative result (absence of analyte) to the most probable number of analyte units in the sample, and which can be used to calculate the probability of each outcome. These have been reviewed by Cochran (1950; Biometrics 5, 105–116). The equations can be incorporated into a computer program in order to generate results tables for the interpretation of tests. From these can be read the most probable number and the relevant confidence limits.

In a modified multi-well plate of the invention, a wall is provided in each well. For example, in a circular well, the dividing wall may be linear, to form two semicircular compartments, or circular, to form an inner and an outer, annular, compartment. Alternatively, the wall between two otherwise discrete wells may have a channel formed therein. If desired, the well may be sub-divided into more than two compartments.

Such a device of the invention may be utilised by introducing a sample into the well, to a level above the dividing wall, so that the sample is the same throughout the well. Then, perhaps after the growth of microorganisms or some other manipulation of the well contents, part of the contents are removed so that the level falls to below that of the wall. There are now two independent samples of the same constitution in each compartment, which can be treated independently, e.g. using one as the basis of an experiment and the other as a control.

BRIEF DESCRIPTION OF THE DRAWINGS

Apparatus of the invention, and suitable for use in carrying out the method of the invention, will now be described by way of example only with reference to the accompanying drawings, in which:

FIG. 1 shows a cover plate 21 adapted to prevent ingress of dust particles during filtration, for an upper manifold 22. The upper manifold 22 has an array of funnels 23 allowing up to 12 individual samples to be introduced into the apparatus. Each array or row of chambers can be separately identified on an indicator panel 24 on the top face of the manifold 22.

Figure 1:
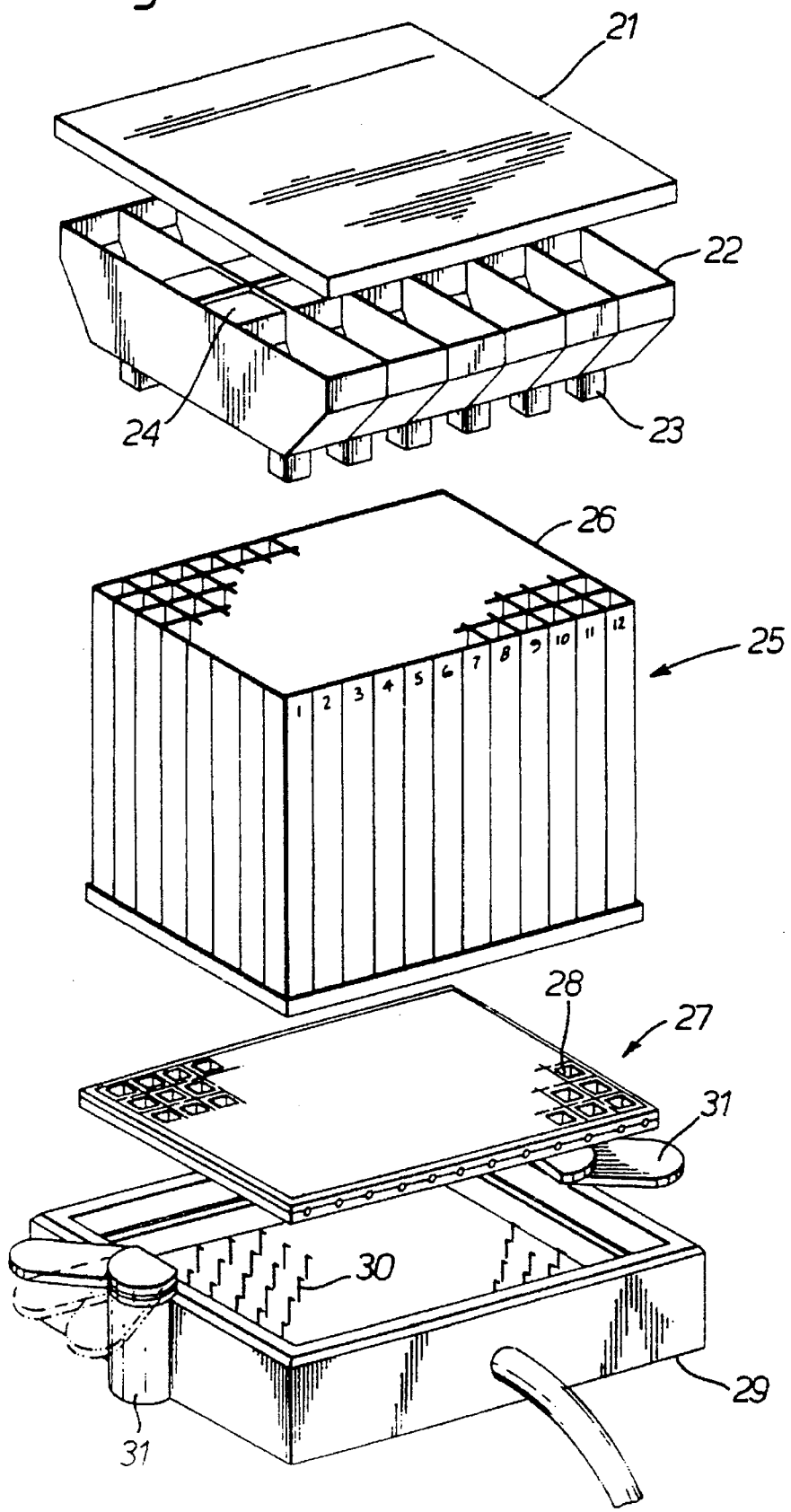
FIG. 1 is an exploded view of one embodiment of the invention.

The upper manifold 22 fits onto the main part 25 of the manifold. This comprises an array of 8×12 vertically elongate chambers 26 (shown as bearing identifying numerals 1–12) into which sample flows on introduction through the upper manifold funnels.

The main manifold 25 acts as a container for liquid sample(s). It itself seats on a multi-well filtration plate 27, the wells 28 again being in an 8×12 array. The filtration plate 27, of conventional type, has filter material at the base of each well. It may be removed, for incubation.

The plate 27 seats on a base member 29 connected by a pipe to a vacuum pump (not shown). The base 29 provides a vacuum chamber and a platform for the filtration plate, with interior pegs 30 supporting the plate 27 and preventing its collapse when suction is applied. The plate 27 is clamped to the base 29 by means of opposed adjustable clamp members 31 providing three positions, i.e. open (for construction or dismantling the device, e.g. for removing the plate 27 for incubation), intermediate and closed, respectively illustrated by solid, dotted and dotted lines.

Figure 2:
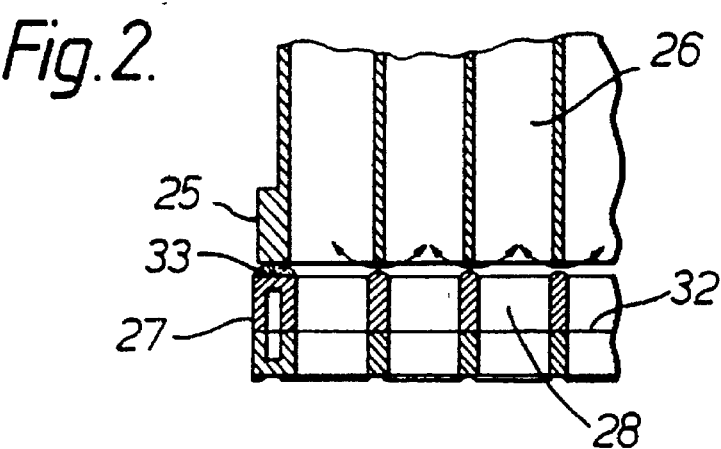
FIGS. 2 and 3 are cross-sectional views, in different positions, of part of the embodiment shown in FIG. 1.
Figure 3:
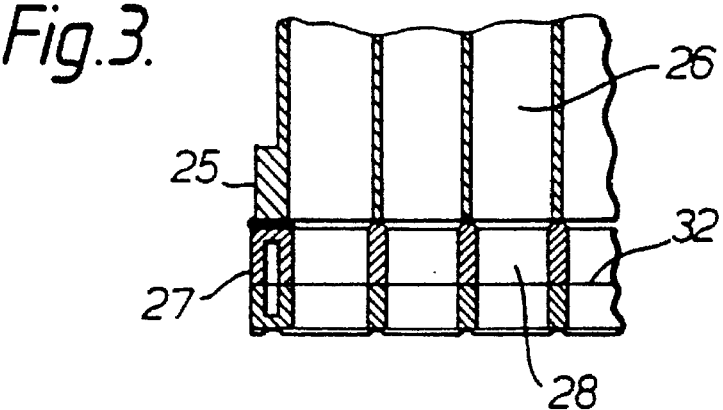

FIGS. 2 and 3 show the points of abutment at respective edges of the main manifold 25 and the filtration plate 27, and shows also the filter membrane 32 forming the base of the wells in the plate 27. A gasket 33 is provided around the edge of the filtration plate, and suitably bound to its top surface.

FIG. 2 shows initial clamping, in the intermediate position of a clamp member 31, such that a gap exists between the manifold 25 and the plate 27, allowing transfer of liquid between the chambers, for equilibration, and as illustrated by arrows. FIG. 3 shows clamping, in the closed position of a clamp member 31, in which each corresponding chamber 26 and well 28 is a discrete volume. The configuration shown in FIG. 3 is adapted to the application of reduced pressure in the base 29, in order to draw liquid through the wells 28.

Figure 4:
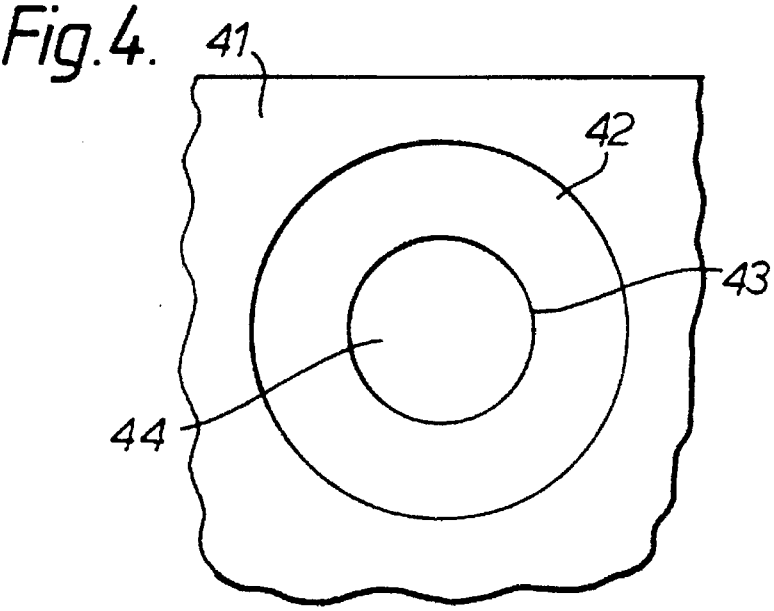
FIG. 4 is a perspective view of part of a modified multi-well plate embodying the present invention.

FIG. 4 shows an individual well of a multi-well plate 41 modified in accordance with the further aspect of this invention. A larger diameter well 42 includes within it a circular wall 43 defining an interior well 44 of lower height.

The following Procedure illustrates the basis for carrying out the method of the invention, to detect e.g. 1–50 microbes in 100 ml (0.01–0.05 cfu/ml). 1 liter or any larger volume may be used.

In order to distribute the sample into several wells, a device as illustrated in FIG. 1 of the drawings is used. The complete procedure may comprise collecting a 100 ml sample in the manifold/container, placing the container and filtration microplate on a suction pump and drawing off liquid, and adding to each well a selected liquid medium that a microbiologist would normally use when carrying out conventional agar plate or liquid culture assays. The microtitre plate is allowed to incubate. Then, the filter may be washed with PBS or similar to remove the medium and any other unwanted chemical components.

Any well which was originally inoculated with one microbe now contains many organisms. The number of organisms present will be dependent on several factors, but the major influence will be the lag time and the doubling rate of the organisms present.

The microtitre plate is then assayed, e.g. using a protocol in which cellular ATP is released and detected by bioluminescence. Assuming that the background from the growth medium is low (for which treatment may be necessary) then the results would be interpreted as a positive for every reading significantly higher than the medium/reagent background. The total of positives gives the minimum number of organisms in the original sample.

In this Procedure, a modified multi-well plate of the invention, e.g. as illustrated in FIG. 4, may be used by adding sufficient medium to each compartment-comprising two wells (42, 44) such that the medium in each compartment is confluent. After incubation, the plate is placed on a suction device, and medium is drawn off. When cells are resuspended ready for assay, the suspension medium is added to the compartment such that there is no overlap of medium between wells, e.g. by drawing off some liquid. In this way, two wells containing cells derived from at least one organism are produced. The contents of one well may be used in the bioluminescence method (which involves killing the microbes, if present, and which may interfere with subsequent tests) while the contents of the other may be used for other tests such as the identification of organisms. In this case, the identification tests can be limited to those wells which showed microbial growth by bioluminescence.

The following Example illustrates how the invention may be used to determine the most probable numbers (MPN) of viable bacteria and ST-producing *E. coli* present in a single sample. Non-specific MPN is achieved by "digital" enumeration by ATP bioluminescence. Specific detection and enumeration of ST enterotoxin is based on the competitive enzyme immunoassay (EIA) format, using a synthetic peptide analogue and a monoclonal antibody to ensure specificity.

EXAMPLE

Bacteria were inoculated into 50 ml flasks of sterile CA-YE broth and grown at 37° C. for 18 h in an orbital incubator. Cultures were diluted in PBS (pH 7.2) to a final concentration of approximately 50 cfu/ml, before adding 50 µl per well of the filter microplate. Three columns of the microplate (24 wells) represented blanks (PBS only); three columns represented diluted ST-producing *E. coli* (NCTC 11603); three columns represented diluted *Salmonella typhimurium* (NCTC 64), used as a negative control; and three columns represented a 1:1 v/v *E. coli/S. typhimurium* diluted sample. After drawing the 50 µl samples through under vacuum, 200 µl CA-YE broth was added to each well. The plate was incubated at 37° C. for 18 hr.

Samples of 1 µl were removed from wells of the incubated filter microplate representing the mixed sample, and streaked onto MacConkey's agar. This medium allowed distinction between mixed and monocultures of *E. coli* and *S. typhimurium*. Lactose-fermenting *E. coli* produce red colonies on MacConkeys agar, whilst non-lactose fermenting *S. typhimurium* produce colourless colonies.

The remaining culture medium was removed under vacuum, and collected in a second microtitre plate for the enterotoxin assay. The filtered microtitre plate was rinsed with 250 µl PBS under vacuum before removing. An ATP bioluminescence assay was performed on the filter plate using a microplate luminometer.

Test and control samples were added to synthetic coated wells at 200 µl per well. Horseradish peroxidase-conjugated anti-toxin antibody was added at 10 µl per well, before mixing and incubating at room temperature for 90 min. After incubation, the contents were aspirated and discarded. Plates were washed five times before adding 100 µl of freshly-prepared phenylenediamine-hydrogen peroxide substrate. After 30 min incubation at room temperature, the reaction was stopped by adding 100 µl 1.5N sulphuric acid. Absorbances (A) were read at 490 nm.

Table 1 gives the ATP bioluminescence results of the diluted bacterial samples cultured in CA-YE broth for 18 h, and thus the MPN. Positive results represent readings of greater than twenty standard deviations above the mean. MPN (most probable number) figures have 95% confidence range.

TABLE 1

| Sample | Positives | MPN |
|---|---|---|
| *E. coli* | 19 out of 24 | 39.2 (21.6–66.0) |
| *S. typhimurium* | 23 out of 24 | 79.5 (38.9–171) |
| Mixed (*E. coli/ S. typhimurium*) | 20 out of 24 | 44.8 (24.6–76.2) |

Table 2 summarises the spread plate results, representing the culture of 1 µl samples on MacConkey's agar from the mixed sample wells of the microtitre plate. The following abbreviations apply: E=*E. coli*; S=*S. typhimurium*; M=mixed (*E. coli* and *S. typhimurium*); B=blank (no growth).

TABLE 2

| | Column | | |
|---|---|---|---|
| Row | 1 | 2 | 3 |
| A | E | E | E |
| B | E | M | S |
| C | E | E | B |
| D | M | E | S |
| E | B | B | M |
| F | E | M | B |
| G | E | M | S |
| H | S | S | E |

The twenty-four wells representing the mixed sample were assayed for enterotoxin. Results of the assay are summarised in Table 3. Positive readings for enterotoxin (+) represent A 490 nm readings of at least 0.5 lower than the negative control value (−=negative for enterotoxin).

TABLE 3

| | Column | | |
|---|---|---|---|
| Row | 1 | 2 | 3 |
| A | + | + | + |
| B | + | + | − |
| C | + | + | − |
| D | + | + | − |
| E | − | − | + |
| F | + | + | − |
| G | + | + | − |
| H | − | − | + |

The Example provides a means of both enumerating the total numbers of viable organisms in a sample, and also specifically detecting and enumerating ST enterotoxin-producing *E. coli*. The enterotoxin assay was capable of detecting the presence of enterotoxin in all wells containing the toxin producing *E. coli*, as shown in Tables 2 and 3. This included the detection of toxin in both monocultures and mixed cultures of bacteria. Those microtitre wells containing either monocultures of *S. typhimurium* or no growth, were all negative for the presence of ST enterotoxin. A MPN of 44.8 cfu/ml (95% confidence range 24.6–76.2) was determined for the mixed sample, whilst 15 of the 24 wells representing this sample contained ST enterotoxigenic *E. coli* (equivalent to MPN of 24.5 cfu/ml).

In summary, this assay provides a rapid, sensitive and reliable technique for the detection of ST enterotoxin in the culture filtrates of a filter microtitre plate.

We claim:

1. A method for analyzing solid material in a liquid sample, which comprises the steps of:

substantially uniformly distributing the sample by passage through a plurality of discrete wells provided in an integral member and whose bases are defined by filter material that retains the solid material and allows the passage of liquid, the concentration of solid material being such that it is absent in at least one well; and analyzing the wells for the presence of retained solid material.

2. A method according to claim 1, in which the solid material is DNA or RNA.

3. A method according to claim 1, in which the solid material comprises microorganisms.

4. A method according to claim 1, which comprises, prior to the analyzing step, the additional step of introducing into the wells a substance that emits a signal in the presence of retained solid material.

5. A method according to claim 4, in which the substance comprises bioluminescence reagents.

6. A method according to claim 4, which comprises the additional step of amplifying the retained solid material, or evidence of its presence.

7. A method according to claim 6, in which the analyzing step comprises adding one or more probes for the solid material, and analyzing the wells for evidence of reaction between a probe and the solid material.

8. A method according to claim 7, for enumerating the solid material, which comprises calculating the number of wells in which solid material is retained as a function of the total number of wells.

9. A method according to claim 8, in which the analyzing step comprises identifying the solid material retained in one or more wells.

10. A method according to claim 1, which comprises the additional step of amplifying the retained solid material, or evidence of its presence.

11. A method according to claim 10, in which the amplifying step comprises introducing a liquid growth medium for the solid material into the wells.

12. A method according to claim 1, in which the analyzing step comprises adding one or more probes for the solid material, and analyzing the wells for evidence of reaction between a probe and the solid material.

13. A method according to claim 1, for enumerating the solid material, which comprises calculating the number of wells in which solid material is retained as a function of the total number of wells.

14. A method according to claim 1, in which the analyzing step comprises identifying the solid material retained in one or more wells.

15. A method according to claim 1, in which the sample passes through the wells under the application of reduced pressure.

16. A method according to claim 1 in which the analyzing step comprises statistical analysis allowing for calculation of a value for a most probable number of microbes per unit volume of liquid sample.

17. A device adapted for use in a method for analyzing solid material in a single liquid sample, which comprises the combination of:

a unit comprising a plurality of discrete wells whose bases are defined by filter material that retains the solid material and allows the passage of liquid under the application of reduced pressure below said unit;

a container for the liquid sample, comprising a plurality of chambers each corresponding to a well;

means for drawing liquid from the container and through the wells under reduced pressure applied below said unit;

means for holding the container relative to the unit, while maintaining a peripheral liquid seal, in either a first fixed position where liquid sample can pass between the chambers above the unit or a second fixed position where each corresponding chamber and well define a discrete volume; and manifold type means providing substantially uniform distribution of the single liquid sample passing from the container into the wells.

* * * * *